US010111630B2

(12) United States Patent
Du et al.

(10) Patent No.: US 10,111,630 B2
(45) Date of Patent: Oct. 30, 2018

(54) X-RAY DIAGNOSIS APPARATUS

(71) Applicant: Toshiba Medical Systems Corporation, Otawara-shi (JP)

(72) Inventors: Rulin Du, Nasushiobara (JP); Seiichirou Nagai, Otawara (JP); Seiichi Nishizuka, Nasushiobara (JP); Shoji Yashiro, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 474 days.

(21) Appl. No.: 14/645,056

(22) Filed: Mar. 11, 2015

(65) Prior Publication Data

US 2015/0271902 A1 Sep. 24, 2015

(30) Foreign Application Priority Data

Mar. 18, 2014 (JP) ................. 2014-054911

(51) Int. Cl.
*A61B 6/00* (2006.01)
*H05G 1/02* (2006.01)
*A61B 6/04* (2006.01)
*A61B 6/06* (2006.01)

(52) U.S. Cl.
CPC .......... *A61B 6/4482* (2013.01); *A61B 6/4452* (2013.01); *A61B 6/4464* (2013.01); *A61B 6/467* (2013.01); *A61B 6/547* (2013.01); *A61B 6/0457* (2013.01); *A61B 6/06* (2013.01); *A61B 6/461* (2013.01)

(58) Field of Classification Search
CPC ... A61B 6/4458; A61B 6/4452; A61B 6/4464; A61B 6/4476; A61B 6/447; A61B 6/045; A61B 6/032
USPC ................................. 378/196–198
See application file for complete search history.

(56) References Cited

U.S. PATENT DOCUMENTS 8,475,041 B2 * 7/2013 Takemoto ............ A61B 6/4476
378/197
9,492,131 B2 * 11/2016 Meek ................... A61B 6/4482

FOREIGN PATENT DOCUMENTS

| JP | 11-137543 A | 5/1999 |
| JP | 2008-200327 | 9/2008 |
| JP | 2010-227376 A | 10/2010 |
| JP | 2014-033800 A | 2/2014 |
| WO | 2011/162149 A1 | 12/2011 |

* cited by examiner

*Primary Examiner* — Don Wong
(74) *Attorney, Agent, or Firm* — Oblon, McClelland, Maier & Neustadt, L.L.P.

(57) ABSTRACT

An X-ray diagnosis apparatus includes a holding device, a drive unit, a route specify unit, an operation direction detector, and a drive controller. The holding device holds an X-ray tube and is configured to be movable. The drive unit is capable of moving the holding device. The route specify unit specifies a movement route from a current position of the holding device to a target position. The operation direction detector detects operation direction, which is the direction of moving operation that the holding device has received. The drive controller controls the drive unit to stop a driving force when the operation direction differs from the direction of the movement route.

11 Claims, 14 Drawing Sheets

FIG. 8A

| OPERATOR ID | ASSOCIATION INFORMATION |
|---|---|
| I1 | T1 |
| I2 | T2 |
| ... | ... |
| In | Tn |

X-RAY DIAGNOSIS APPARATUS

CROSS-REFERENCE TO RELATED APPLICATION

This application is based upon and claims the benefit of priority from Japanese Patent Application No. 2014-054911, filed Mar. 18, 2014; the entire contents of which are incorporated herein by reference.

FIELD

Embodiments described herein relate generally to an X-ray diagnosis apparatus.

BACKGROUND

In the radiography of a subject with X-ray equipment such as an X-ray diagnosis apparatus, it is required to capture images of the subject at various angles to obtain effective information from the subject. Accordingly, the holding device of an X-ray tube needs to be adjusted variously in its position and angle. This position/angle adjustment of the holding device is performed manually or automatically.

However, manual positioning requires enough force to move the heavy holding device. On the other hand, automatic positioning moves the holding device at slow speed and takes more time than the manual positioning does.

BRIEF DESCRIPTION OF THE DRAWINGS

FIG. 8A is a schematic diagram of association information for each operator ID in an X-ray diagnosis apparatus according to a first modification of the first embodiment.

DETAILED DESCRIPTION

In general, according to one embodiment, an X-ray diagnosis apparatus includes a holding device, a drive unit, a route specify unit, an operation direction detector, and a drive controller. The holding device holds an X-ray tube and is configured to be movable. The drive unit is capable of moving the holding device. The route specify unit is configured to specify a movement route from a current position of the holding device to a target position. The operation direction detector is configured to detect operation direction, which is the direction of moving operation that the holding device has received. The drive controller is configured to control the drive unit to stop a driving force when the operation direction differs from the direction of the movement route.

First Embodiment

Configuration

Figure 1:
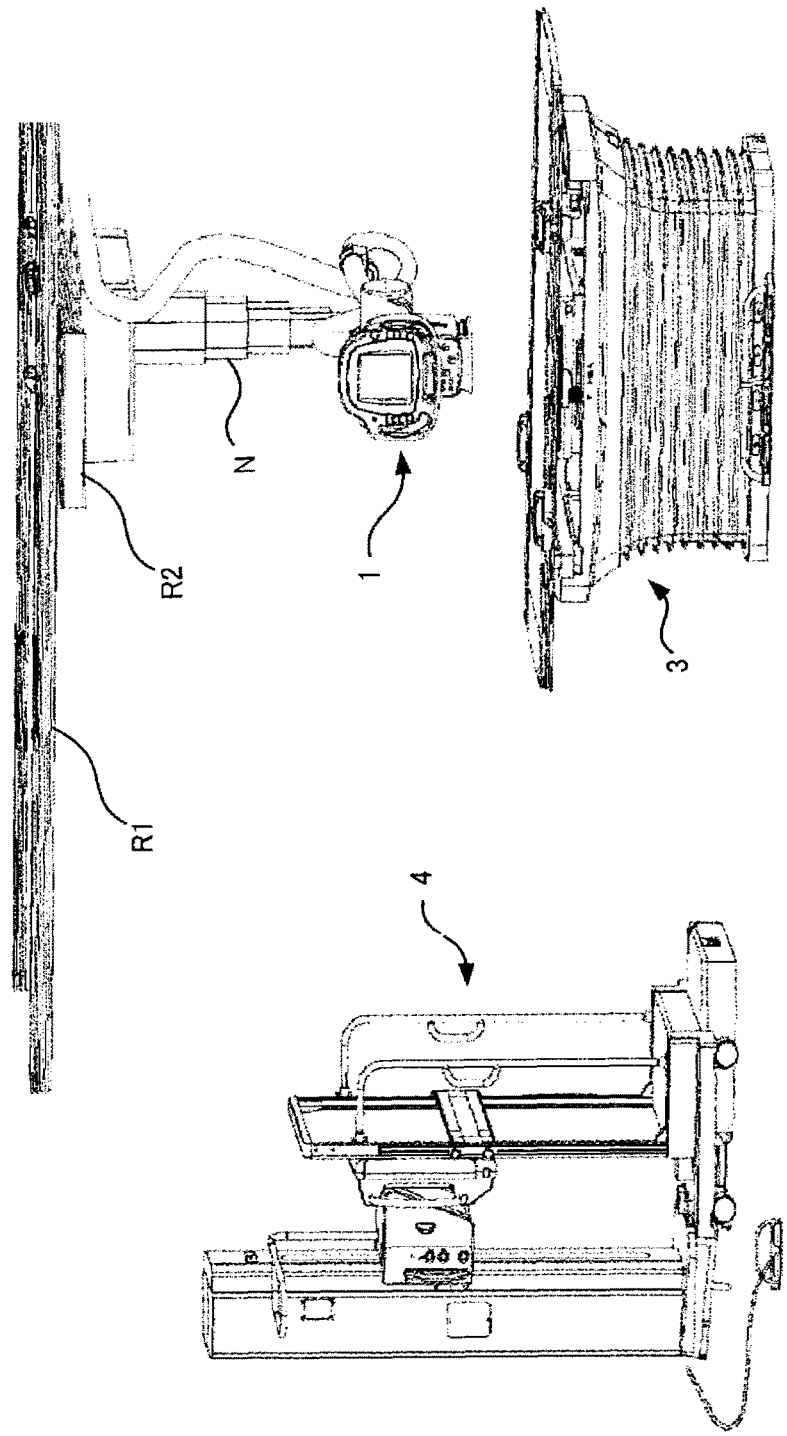
FIG. 1 is a schematic exterior view of an X-ray diagnosis apparatus according to a first embodiment.
Figure 2:
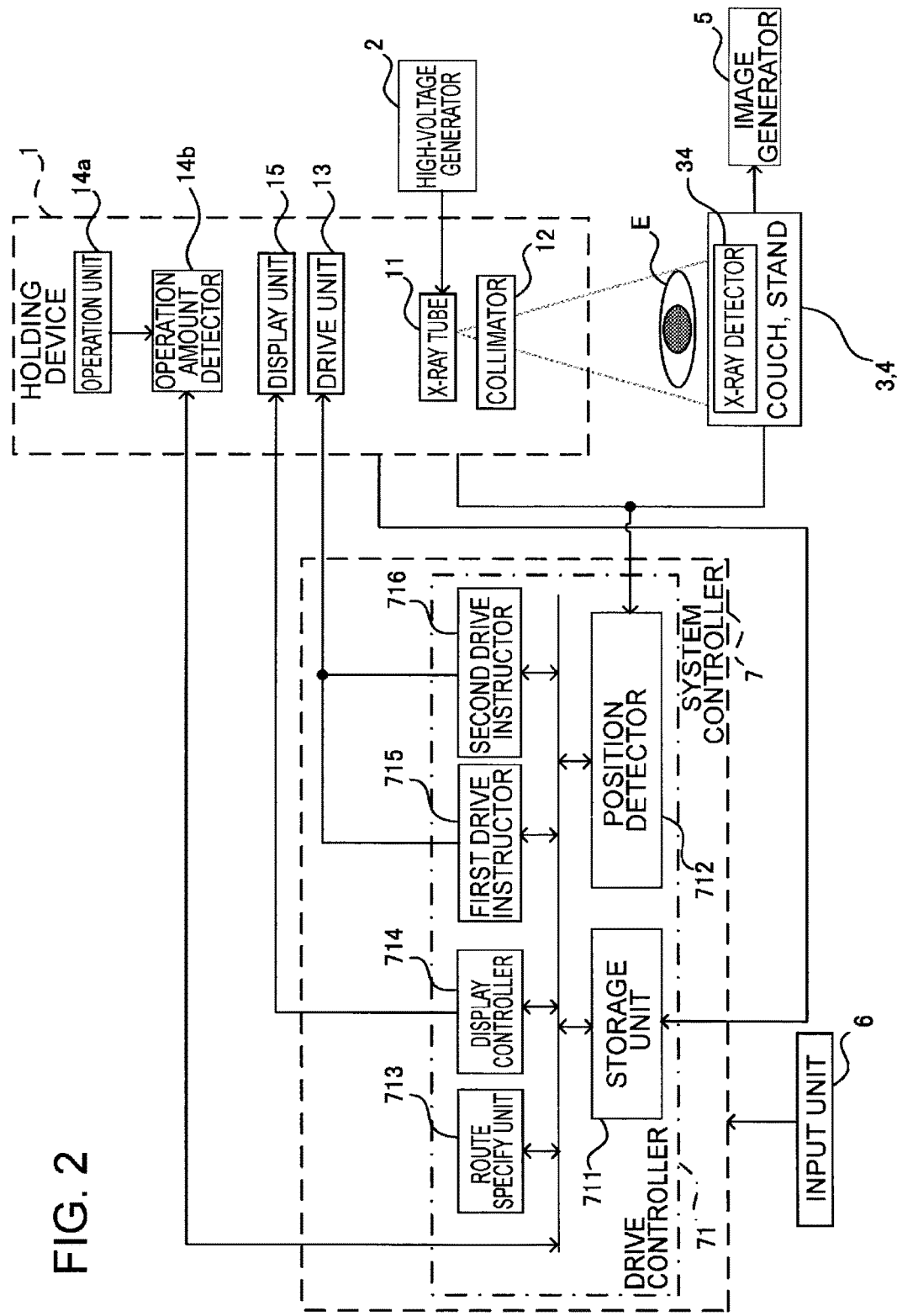
FIG. 2 is a block diagram of the X-ray diagnosis apparatus of the first embodiment.
Figure 3:
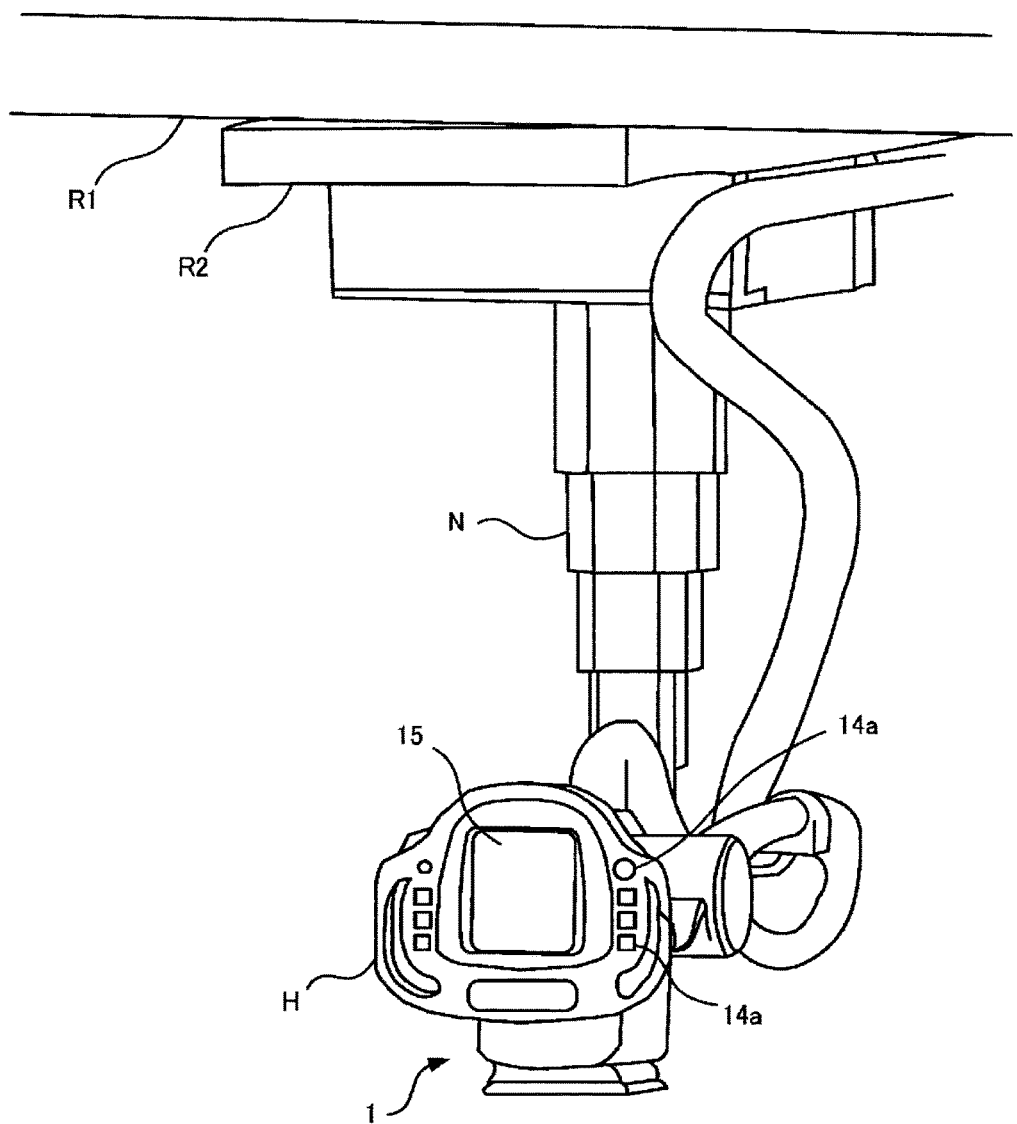
FIG. 3 is a schematic exterior view of the X-ray diagnosis apparatus of the first embodiment.

Referring to FIGS. 1, 2, and 3, a description is given of the configuration of an X-ray diagnosis apparatus according to a first embodiment. The X-ray diagnosis apparatus includes a holding device 1, a high-voltage generator 2, a couch 3, a stand 4, an image generator 5, an input unit 6, and a system controller 7.

(Holding Device 1)

The holding device 1 holds an X-ray tube 11. The holding device 1 is configured to be movable. The holding device 1 includes the X-ray tube 11, a collimator 12, a drive unit 13, an operation unit 14a, an operation amount detector 14b, and a display unit 15.

The X-ray tube 11 generates X-rays. The X-ray tube 11 has an anode and a cathode. The cathode emits electrons. The anode emits X-rays as a result of being struck by the electrons from the cathode, thus irradiating a subject with the X-rays.

The collimator 12 forms a slit (opening). By changing the size and shape of the slit, the collimator 12 adjusts the radiation field of the X-rays generated by the X-ray tube 11.

The drive unit 13 is configured to be capable of moving the holding device 1. For example, the drive unit 13 includes drive mechanisms such as a motor, a gear, a clutch, and the like. Thereby, the drive unit 13 can horizontally move the holding device 1 along rails R1 and R2. The drive unit 13 may vertically move the holding device 1 by extending and contracting a neck N. The drive unit 13 may change the X-ray emitting direction by rotating the holding device 1. The movements of the holding device 1 caused by the drive unit 13 include at least one of horizontal move, vertical move, and rotation.

The operation unit 14a is configured to be capable of receiving operator's operations including driving operation. The term "driving operation" as used herein refers to an operation for controlling the driving force of the drive unit 13. For example, the operation unit 14a includes a button switch that can be pressed as the driving operation. The operation unit 14a is located near an operation handle H. The operation unit 14a may be integrated with the operation handle H. The operation amount detector 14b detects an operation amount indicating the strength of driving operation received by the operation unit 14a. The operation amount detector 14b may be, for example, a pressure sensor. The pressure sensor detects pressure corresponding to the magnitude of pressing force. Here, the magnitude of pressing force corresponds to the strength of driving operation, and the pressure corresponds to the operation amount. The operation amount detector 14b feeds a drive controller 71 with the detected pressure as an operation amount.

The display unit 15 displays movement direction information indicating a direction in which the holding device 1 is to be moved (details are described below). The display unit 15 may display driving force information indicating the magnitude of a driving force. The display unit 15 includes a display device such as a liquid crystal display (LCD), an organic electro-luminescence (EL) display, or the like.

(High-Voltage Generator 2)

The high-voltage generator 2 generates high voltages for the X-ray tube 11 to emit X-rays. The high-voltage generator 2 applies a high voltage across the anode and cathode of the X-ray tube 11.

(Couch 3 and Stand 4)

The couch 3 is used as a radiographic table on which a subject is lying in radiography. The stand 4 is used as a radiographic stand that a subject stands on in radiography. The couch 3 and the stand 4 include an X-ray detector 34.

The X-ray detector 34 detects an X-ray that has passed through a subject E. For example, the X-ray detector 34 converts detected X-rays to electric charges to store the charges. The X-ray detector 34 outputs the charges thus stored to the image generator 5 as detection data.

(Image Generator 5)

The image generator 5 generates an X-ray image based on the detection data from the X-ray detector 34. Thereby, the X-ray image representing the structure of the subject E is obtained. The image generator 5 includes a memory area to store the X-ray image.

(Input Unit 6)

The input unit 6 receives input operation by an operator, and feeds each unit of the apparatus with information according to the input operation. The input unit 6 includes, for example, a keyboard, a mouse, and the like.

(System Controller 7)

The system controller 7 controls each unit of the X-ray diagnosis apparatus. The system controller 7 stores a computer program to implement the functions of each unit of the apparatus. By executing the computer program, the system controller 7 implements the functions of each unit. The system controller 7 includes the drive controller 71.

The drive controller 71 controls the drive unit 13 based on an operation amount detected by the operation amount detector 14b. The drive controller 71 includes a storage unit 711, a position detector 712, a route specify unit 713, a display controller 714, a first drive instructor 715, and a second drive instructor 716.

The storage unit 711 stores a predetermined range to associate the operation amount of driving operation received by the operation unit 14a with a driving force output by the drive unit 13. The predetermined range is determined in advance. The first drive instructor 715 instructs the drive unit 13 to output a driving force to move the holding device 1 while the operation amount is within the predetermined range.

Figure 4:
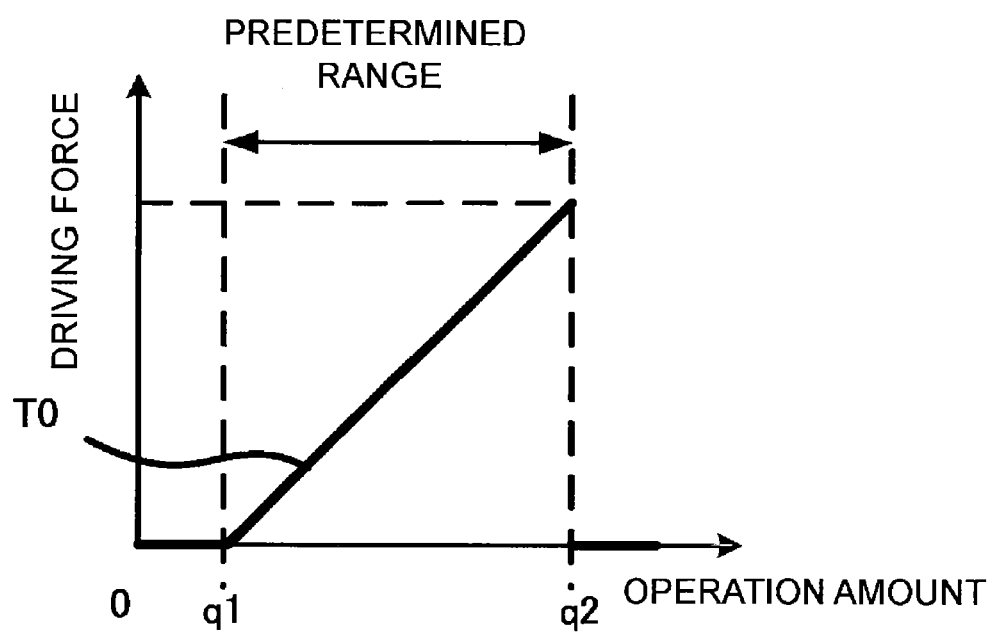
FIG. 4 is a schematic diagram of association information in the X-ray diagnosis apparatus of the first embodiment.

For example, the storage unit 711 stores, in advance, association information that associates the operation amount with the driving force in a proportional relationship in the predetermined range. FIG. 4 is a schematic diagram of association information T0. In FIG. 4, the horizontal axis indicates the operation amount, while the vertical axis indicates the driving force. In addition to the association information T0, a lower limit value q1 and an upper limit value q2 of the predetermined range are input in advance to the storage unit 711 through the input unit 6. A value larger than zero may sometimes be input as the lower limit value q1 of the predetermined range. In this case, the range from zero to the lower limit value q1 functions as a dead zone to prevent a malfunction that may be caused when the operator erroneously touches the button switch. Incidentally, the operation amount and the driving force may not necessarily be associated in a proportional relationship. For example, the driving force may be associated with the operation amount in a relationship where the driving force monotonically increases with respect to the operation amount in the predetermined range.

While an operation amount is in the predetermined range, the first drive instructor 715 controls the drive unit 13 to output a driving force associated with the operation amount based on the association information T0. For example, having received an operation amount detected by the operation amount detector 14b, the first drive instructor 715 retrieves the association information T0 from the storage unit 711. Referring to the association information T0 with the operation amount, the first drive instructor 715 feeds the drive unit 13 with an instruction signal that indicates a driving force associated with the operation amount as long as the operation amount is in the predetermined range. In response to the instruction signal, the drive unit 13 outputs the driving force indicated by the signal to move the holding device 1. On this occasion, the drive unit 13 connects clutches to drive a motor with an output corresponding to the driving force, thereby generating the driving force. The upper limit of the driving force in the association information T0 is designed as appropriate according to the characteristics of the motor and the like of the drive unit 13.

In reference to the association information T0 with the operation amount, if the operation amount falls out of the predetermined range, the first drive instructor 715 outputs an instruction signal to the drive unit 13 to stop the output of the driving force. In response to the instruction signal, the drive unit 13 disconnects the clutches to stop the driving force. With this, the holding device 1 can be manually moved (can receive manual moving operation) by the operator. The drive unit 13 may stop the motor upon disconnecting the clutches.

Besides, the storage unit 711 stores a target position of the holding device 1. The target position is the position of the holding device 1 when X-rays are taken in X-ray diagnosis. The target position is input in advance to the storage unit 711 depending on the components of the X-ray diagnosis. The storage unit 711 may store a plurality of positions. In this case, the storage unit 711 receives selection operation through the input unit 6, and stores one selected from the positions as the target position in the X-ray diagnosis.

The position detector 712 detects the current position of the holding device 1. For example, the position detector 712 detects the position of the holding device 1 in a direction parallel to the rails R1 and R2, and also detects the length of the neck N, thereby detecting the current position of the holding device 1. The position detector 712 feeds the route specify unit 713 with current position information indicating the detected current position. As well as retrieving the target position from the storage unit 711, the route specify unit 713 receives the current position information from the position detector 712. The route specify unit 713 specifies a movement route from the current position indicated by the current position information to the target position. For example, as the movement route, the route specify unit 713 specifies a route to horizontally move the holding device 1, then specifies a route to vertically move the holding device 1, and specifies a route to rotate the holding device 1. The route specify unit 713 may specify the movement route using horizontal, vertical, and rotating routes appropriately alone or in combination. The direction of the movement route (movement direction) extends in a direction to be close to the target position and along the specified routes. The route specify unit 713 feeds the display controller 714 and the first drive instructor 715 with movement direction information indicating the movement direction.

While an operation amount is in the predetermined range, the first drive instructor 715 sequentially controls the drive unit 13 to move the holding device 1 toward the target position based on the target position and the current position detected by the position detector 712. For example, the first drive instructor 715 sequentially controls the drive unit 13 to move the holding device 1 in the movement direction indicated by the movement direction information from the route specify unit 713. With this, the drive unit 13 rotates the motor in relation to each driving shaft to move the holding device 1 in the movement direction.

Under the control of the second drive instructor 716, the drive unit 13 outputs a predetermined second driving force. The magnitude of the second driving force is determined in advance as a constant value. The magnitude of the second driving force may be determined by selecting a value from a plurality of predetermined magnitudes of the second driving force. The second drive instructor 716 moves the holding device 1 according to general movement control for the holding device.

Described below is the difference between the movement of the holding device 1 by the first drive instructor 715 and that by the second drive instructor 716. The first drive instructor 715 exerts the movement control when the operation unit 14a receives operator's driving operation. In this embodiment, while the operator is pressing the button switch of the operation unit 14a (driving operation), the first drive instructor 715 performs the movement control.

On the other hand, the second drive instructor 716 exerts the movement control without operator's driving operation on the operation unit 14a. In this embodiment, regardless of whether the operator presses the button switch of the operation unit 14a (driving operation), the second drive instructor 716 performs the movement control.

The operation unit 14a includes a switch to switch the movement control between the first drive instructor 715 and the second drive instructor 716. When the movement control of the second drive instructor 716 is turned on via the switch, the second drive instructor 716 controls the drive unit 13 to output the second driving force. The movement control of the second drive instructor 716 may be turned on when the holding device 1 moves within a predetermined distance from the target position.

Figure 5:
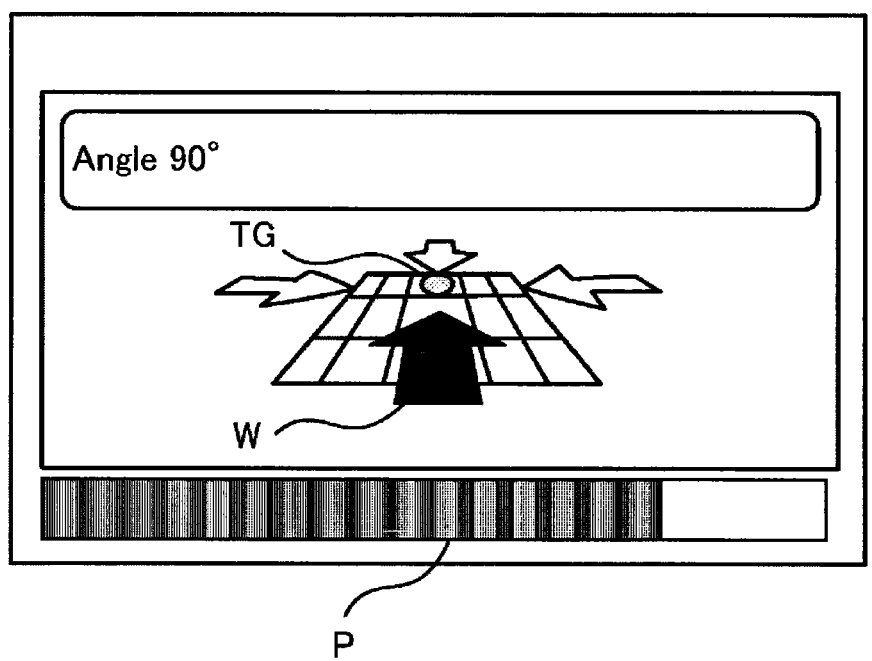
FIG. 5 is a schematic diagram of a display screen of a display unit of the X-ray diagnosis apparatus of the first embodiment.

The display controller 714 displays on the display unit 15 movement direction information indicating a direction in which the holding device 1 is to be moved. FIG. 5 is a schematic diagram of the display screen of the display unit 15. In the example of FIG. 5, the black arrow represents movement direction information W that indicates a movement direction toward a position marker TG indicating the target position. In this example, the movement direction information W indicates that the movement direction of the holding device 1 extends from the front to the back of the figure. The display controller 714 displays on the display unit 15 driving force information P that indicates the magnitude of the driving force. In the example of FIG. 5, the driving force information P is displayed as a horizontal meter. The movement direction information W is only required to be displayed in such a manner as to indicate the movement direction, and is not limited to the arrow. Similarly, the driving force information P is only required to be displayed in such a manner as to indicate the magnitude of a driving force, and is not limited to the meter.

Operation

Figure 6:
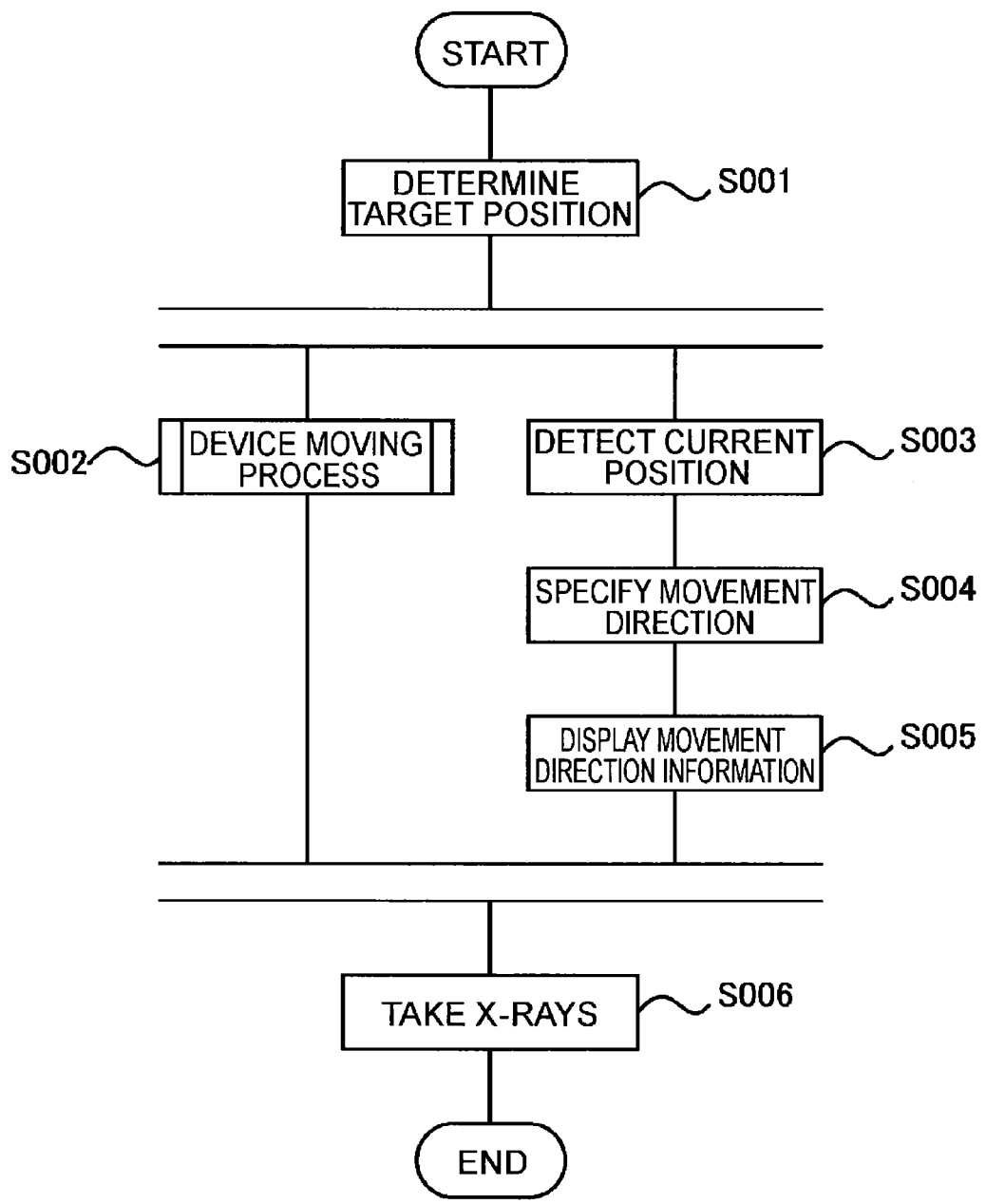
FIG. 6 is a flowchart of the operation of the X-ray diagnosis apparatus of the first embodiment.
Figure 7:
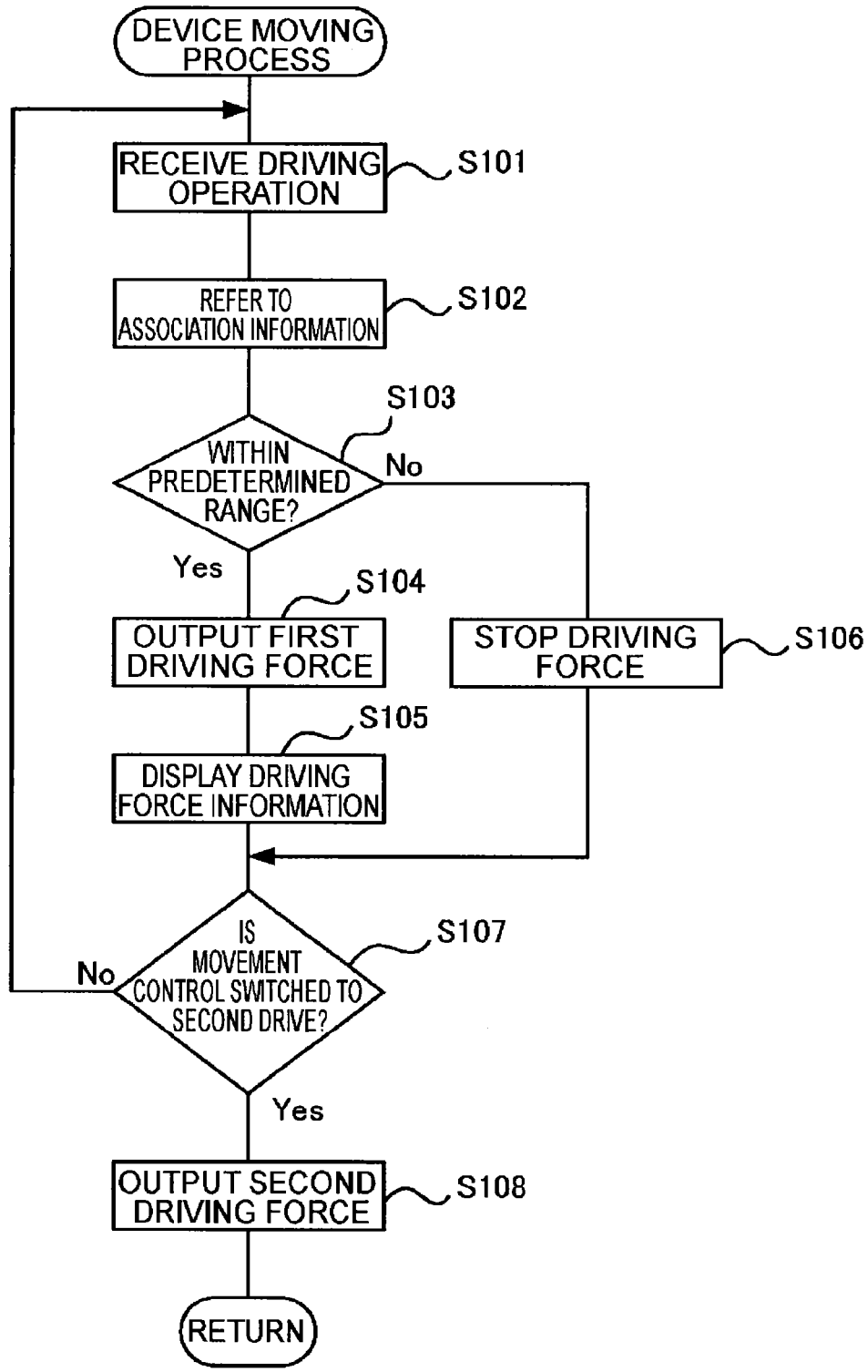
FIG. 7 is a flowchart of the operation of the X-ray diagnosis apparatus of the first embodiment.

FIG. 6 is a flowchart of the operation of the X-ray diagnosis apparatus of the embodiment.
(Step S001)
The storage unit 711 receives input of a target position, and stores the target position therein. Incidentally, the storage unit 711 may store a plurality of positions and store one selected from the positions as the target position in the X-ray diagnosis.
(Step S002)
The holding device 1 moves to the target position. Details of this device moving process are illustrated in FIG. 7.
(Step S003)
The position detector 712 detects the current position of the holding device 1. The position detector 712 feeds the route specify unit 713 with current position information indicating the current position.
(Step S004)
The route specify unit 713 retrieves the target position from the storage unit 711 as well as receiving the current position information from the position detector 712. The route specify unit 713 specifies a movement route from the current position indicated by the current position information to the target position. The route specify unit 713 feeds the display controller 714 and the first drive instructor 715 with movement direction information indicating the direction of the movement route (movement direction).
(Step S005)
The display controller 714 displays the movement direction information received from the route specify unit 713 on the display unit 15.

Incidentally, step S002 and steps S003 to S005 are performed in parallel. That is, while the holding device 1 is moving, the position detector 712 detects the current position of the holding device 1, the route specify unit 713 specifies the direction of the movement route, and the display controller 714 displays the movement direction information on the display unit 15, at a predetermined sampling rate, simultaneously in parallel.
(Step S006)
In response to operator's operation to start radiography, the X-ray diagnosis apparatus takes X-rays. At this time, the X-ray tube 11 emits X-rays to irradiate the subject E with the X-rays. The X-ray detector 34 detects an X-ray that has passed through the subject E, and outputs detection data to the image generator 5. The image generator 5 generates an X-ray image based on the detection data from the X-ray detector 34.

FIG. 7 is a flowchart of the device moving process for moving the holding device 1 of the embodiment (step S002 in FIG. 6).
(Step S101)
The operation unit 14a receives operator's driving operation. The operation amount detector 14b detects an operation amount indicating the strength of the driving operation received. The operation amount detector 14b outputs the operation amount to the first drive instructor 715.
(Step S102)
Having received the operation amount detected by the operation amount detector 14b, the first drive instructor 715 retrieves the association information T0 from the storage unit 711. The first drive instructor 715 refers to the association information T0 with the operation amount.
(Step S103)
The first drive instructor 715 determines whether the operation amount is in a predetermined range. If the operation amount is in the predetermined range (Yes in step S103), the process moves to step S104. On the other hand, if the operation amount is out of the predetermined range (No in step S103), the process moves to step S106.

(Step S104)

While the operation amount is in the predetermined range, the first drive instructor 715 feeds the drive unit 13 and the display controller 714 with an instruction signal indicating a driving force associated with the operation amount. In response to the instruction signal, the drive unit 13 outputs the driving force (first driving force) indicated by the signal to move the holding device 1.

(Step S105)

Having received the instruction signal from the first drive instructor 715, the display controller 714 displays driving force information that indicates the driving force (see FIG. 5) on the display unit 15.

(Step S106)

The first drive instructor 715 outputs an instruction signal to the drive unit 13 to stop the output of the driving force. In response to the instruction signal, the drive unit 13 stops the driving force. With this, the holding device 1 can be manually moved by the operator. Incidentally, the operation amount falls out of the predetermined range when, for example, the button switch is pressed with a pressure of the lower limit value q1 of the predetermined range or less, or is not pressed, or it is pressed with a pressure of the upper limit value q2 of the predetermined range or greater to move the holding device 1 with a force exceeding the output limit of the motor (see FIG. 4).

(Step S107)

If the movement control of the second drive instructor 716 is turned on (Yes in step S107), for example, when the switch is pressed during the movement control of the first drive instructor 715, the process moves to step S108. The process may move to step S108 when the holding device 1 moves within a predetermined distance from the target position. If the movement control of the second drive instructor 716 is not turned on (No in step S107), the process returns to step S101.

(Step S108)

The second drive instructor 716 feeds the drive unit 13 with an instruction signal indicating a predetermined second driving force. With this, the drive unit 13 moves the holding device 1 toward the target position with the second driving force, thereby placing the holding device 1 in the target position.

According to the first embodiment, the X-ray diagnosis apparatus includes the holding device 1, the drive unit 13, the operation amount detector 14b, and the drive controller 71. The holding device 1 holds the X-ray tube 11, and is configured to be movable. The drive unit 13 is configured to be capable of moving the holding device 1. The operation amount detector 14b detects an operation amount indicating the strength of driving operation. The drive controller 71 controls a driving force output from the drive unit 13 based on the operation amount. In this manner, the X-ray diagnosis apparatus of this embodiment moves the holding device 1 with the driving force that is controlled based on the strength of driving operation. Accordingly, the operator can move the holding device 1 with a desired driving force while adjusting the pressing force on the button switch of the operation unit 14a. Thus, the positioning of the holding device 1 can be facilitated.

Besides, the drive controller 71 may store a predetermined range, and control the drive unit 13 to output a driving force for moving the holding device 1 according to the operation amount while an operation amount is in the predetermined range. When the operation amount falls out of the predetermined range, the drive controller 71 may control the drive unit 13 to stop the driving force. With this, the operator can move the holding device 1 automatically while adjusting the pressing force on the button switch so that the operation amount falls within the predetermined range. The operator can also move the holding device 1 manually by pressing the button switch hard so that the operation amount falls out of the predetermined range. In addition, the operator can move the holding device 1 manually by releasing the hand from the button switch for disconnecting the clutches to stop the driving force. For example, if the operator prefers more speed even when the holding device 1 is moved at the maximum speed of the driving function of the drive unit 13, the operator can switch the automatic operation to manual one by pressing the button switch with a force of the upper limit value q2 of the predetermined range or greater (see FIG. 4). Thus, the operator can manually make a quick move of the holding device 1. Moreover, since the operation unit 14a is located near the operation handle H of the holding device 1, the operator can easily switch between automatic and manual operation while touching both the operation handle H and the operation unit 14a. This further facilitates the positioning of the holding device 1.

The drive controller 71 may store, in advance, the association information T0 that associates the operation amount with the driving force in a proportional relationship in a predetermined range. While an operation amount is in the predetermined range, the drive controller 71 may control the drive unit 13 to output a driving force associated with the operation amount based on the association information T0. With this, the operator can move the holding device 1 with a desired driving force output by the drive unit 13 by adjusting the operation amount such as the pressing force on the button switch and the like. Thus, the holding device 1 can be moved by easy adjustment of the driving force.

The drive controller 71 may include the storage unit 711 and the position detector 712. The storage unit 711 stores a target position of the holding device 1. The position detector 712 detects the current position of the holding device 1. While an operation amount is in a predetermined range, the drive controller 71 sequentially controls the drive unit 13 to move the holding device 1 in a movement direction based on the target position and the current position detected by the position detector 712. As described above, the X-ray diagnosis apparatus of the embodiment moves the holding device 1 in the movement direction while the operation amount is in the predetermined range. For example, in preparation for X-ray diagnosis, when the operator stops the output of the drive unit 13 by pressing hard the button switch of the operation unit 14a and manually moves the holding device 1, the holding device 1 may sometimes deviate from the movement route at the start of the movement. Even in such a case, the holding device 1 can be moved automatically in the movement direction by operator's adjustment of the pressing force on the button switch in the predetermined range.

The holding device 1 may include the display unit 15. In this case, the drive controller 71 displays on the display unit 15 movement direction information indicating a direction in which the holding device 1 is to be moved. This allows the operator to easily and visually check the movement direction of the holding device 1. In addition, the movement direction of the holding device 1 is determined in advance, and while the drive unit 13 is outputting a driving force, the holding device 1 moves in the movement direction displayed on the display unit 15. This reduces the risk of the holding device 1 moving in an unintended direction, and thus, the holding device 1 can be moved safely.

If the holding device 1 includes the display unit 15, the drive controller 71 may display on the display unit 15 driving force information that indicates the magnitude of a driving force. With this, the operator can easily adjust the operation amount while visually checking the driving force information displayed on the display unit 15.

First Modification

Described below is an X-ray diagnosis apparatus according to a first modification of the first embodiment. The X-ray diagnosis apparatus of this modification is different from that of the first embodiment in the configuration of the drive controller. In the following, the differences are mainly described.

Figure 8B:
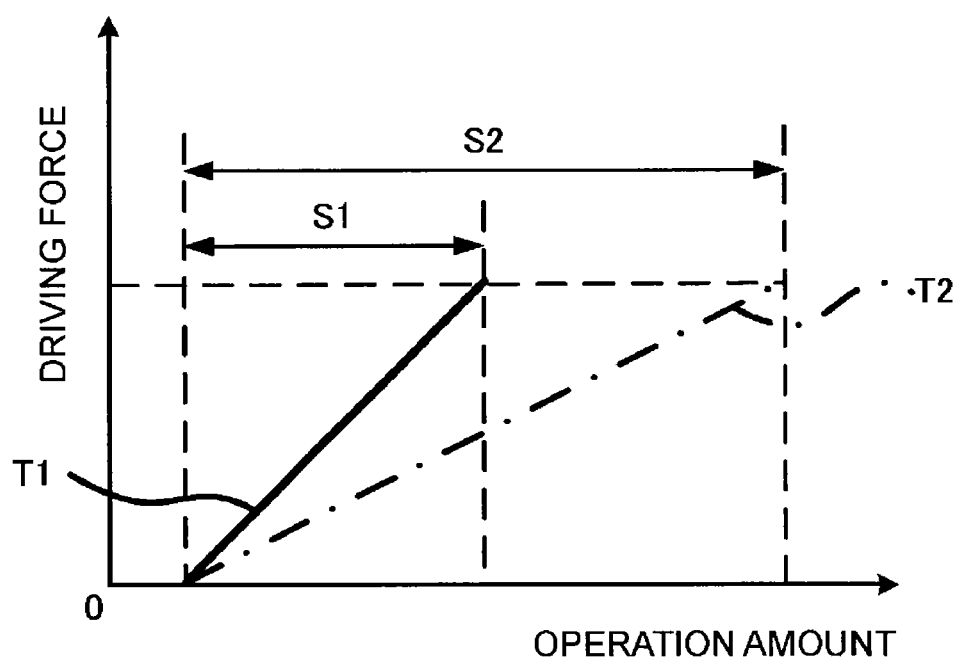
FIG. 8B is a schematic diagram of the association information for each operator ID in the X-ray diagnosis apparatus of the first modification.

The storage unit 711 stores in advance association information with respect to each operator ID that uniquely identifies the operator. FIGS. 8A and 8B are schematic diagrams of the association information for each operator ID. In the example of FIG. 8A, the storage unit 711 stores in advance association information T1, T2, . . . , Tn with respect to each of operator IDs I1, I2, . . . , In (n: a predetermined natural number). The value of the predetermined natural number n is designed as appropriate according to the capacity of the storage unit 711. FIG. 8B schematically illustrates the association information T1 for the operator I1 and the association information T2 for the operator I2. In FIG. 8B, the horizontal axis indicates the operation amount, while the vertical axis indicates the driving force. In the association information T1, the operation amount and the diving force are associated in a proportional relationship at a steeper angle as compared to the association information T2. In addition, a predetermined range S1 of the association information T1 is set narrower than a predetermined range S2 of the association information T2. This indicates that the operator I1 achieves output of a higher driving force with less operation amount as compared to the operator I2. The association information for each operator ID is input in advance in the storage unit 711 through, for example, the input unit 6.

For example, upon receipt of selection operation to select an operator ID via the input unit 6, the storage unit 711 specifies association information of the operator ID as association information used to move the holding device 1. While the operation amount is in the predetermined range, the first drive instructor 715 controls the drive unit 13 based on the association information of the operator ID selected by the selection operation received through the input unit 6.

According to this modification, association information is stored in advance with respect to each operator. The holding device is moved by a driving force of a magnitude based on association information of a selected operator. Thus, the operator can move the holding device while adjusting the operation amount based on association information according to, for example, his/her own grip strength and arm strength.

Second Modification

The X-ray diagnosis apparatus of this modification is different from that of the first embodiment in the configuration of the drive controller and the holding device. The differences are mainly described below.

Figure 9:
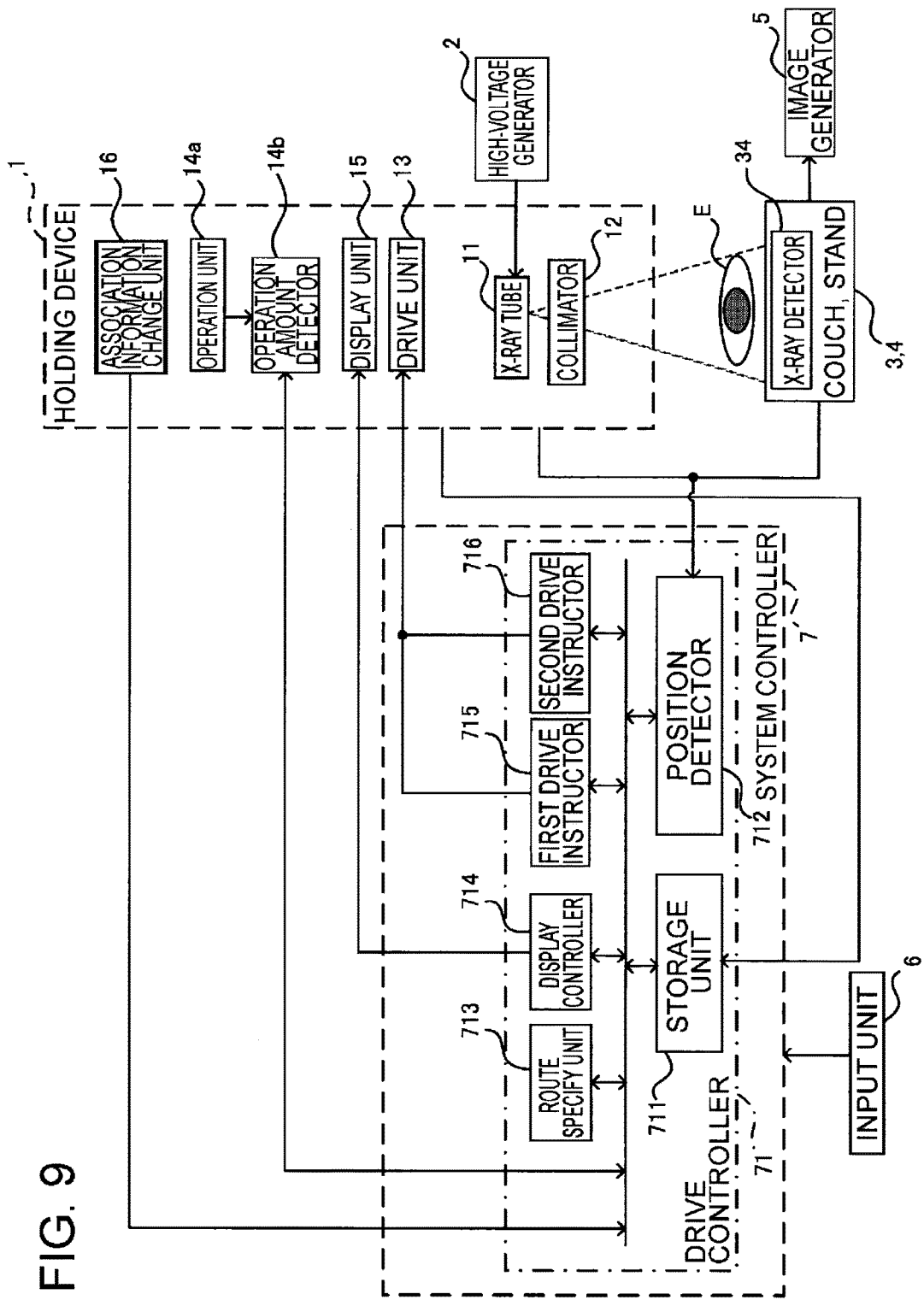
FIG. 9 is a block diagram of an X-ray diagnosis apparatus according to a second modification.

FIG. 9 is a block diagram of an X-ray diagnosis apparatus according to the second modification. As illustrated in FIG. 9, the holding device 1 includes an association information change unit 16. The association information change unit 16 is configured to be capable of changing association information upon receipt of change operation to change the association information. The association information change unit 16 is located near the operation unit 14a.

Figure 10A:
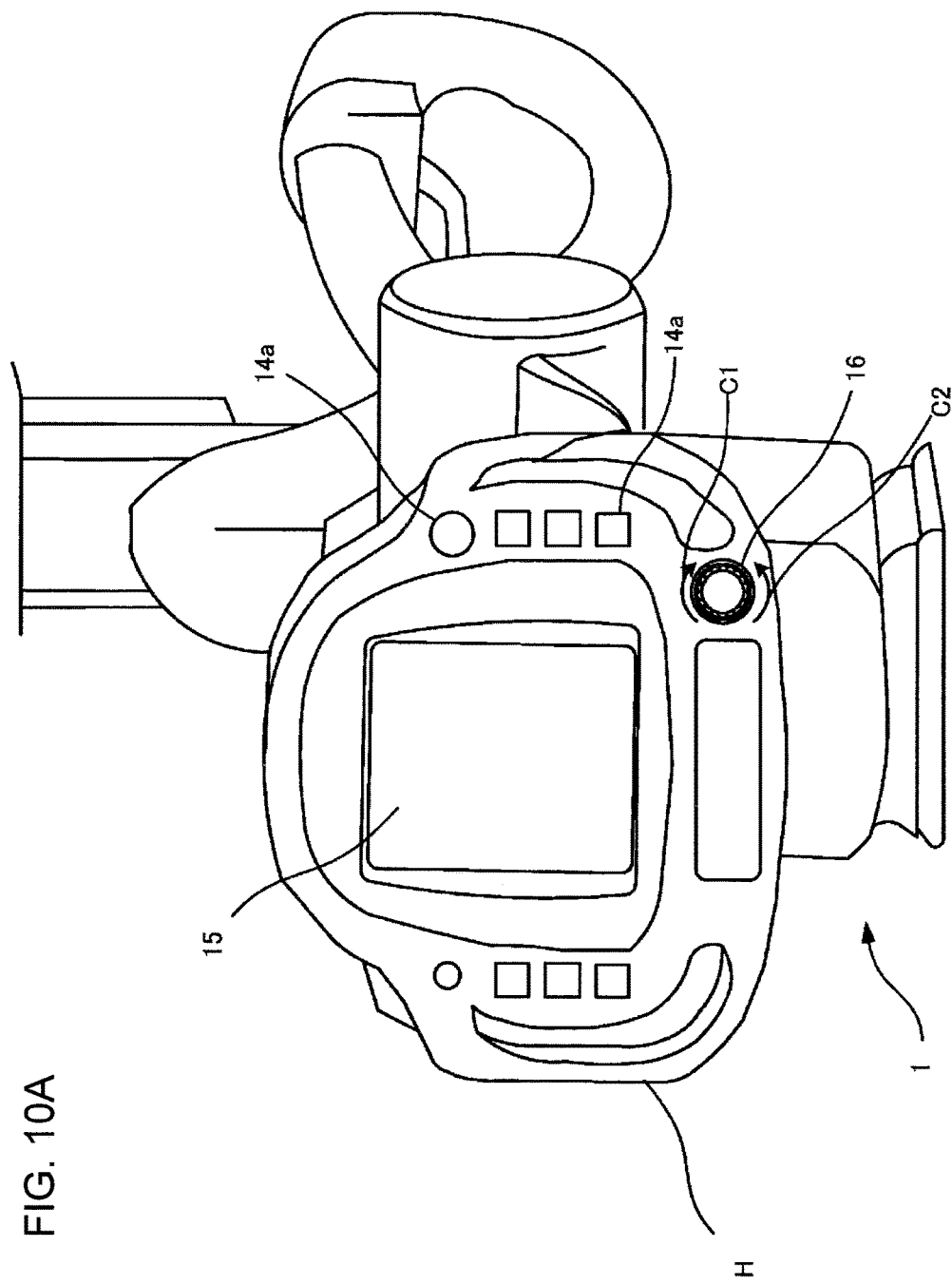
FIG. 10A is a schematic diagram of an association information change unit of the second modification.
Figure 10B:
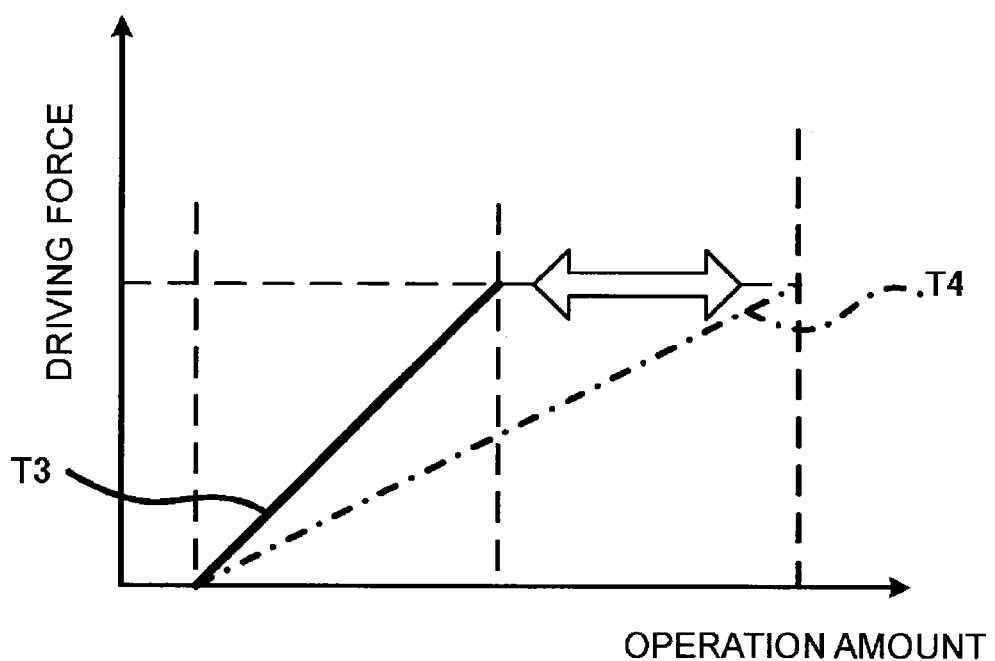
FIG. 10B is a schematic diagram of association information that is changed by the association information change unit of the second modification.

FIG. 10A is a schematic diagram of the association information change unit 16. For example, the association information change unit 16 is configured to be rotatable as a rotating dial. According to the direction and amount of change operation received, the association information change unit 16 changes the gradient of association information. FIG. 10B is a schematic diagram of association information that is changed in response to change operation received by the association information change unit 16. For example, when rotated in a direction C1 as change operation while the association information T3 is being used, the information change unit 16 changes association information to be used so that the information comes close to the association information T4 from the association information T3 according to the rotation amount of the change operation. On the other hand, if rotated in a direction C2 opposite to the direction C1 as change operation while the association information T4 is being used, the association information change unit 16 changes association information to be used so that the information comes close to the association information T3 from the association information T4 according to the rotation amount of the change operation. While the operation amount is in the predetermined range, the first drive instructor 715 controls the drive unit 13 based on new association information obtained by the information change unit 16.

Upon moving the holding device 1, the operator may sometimes wish to change association information depending on his/her fatigued state. According to this modification, the X-ray diagnosis apparatus includes the association information change unit 16 configured to receive change operation to change the association information, thus enabling changes in association information. Hence, the operator can move the holding device 1 while changing an association relationship between the operation amount and the driving force with ease.

Second Embodiment

Configuration

Figure 11:
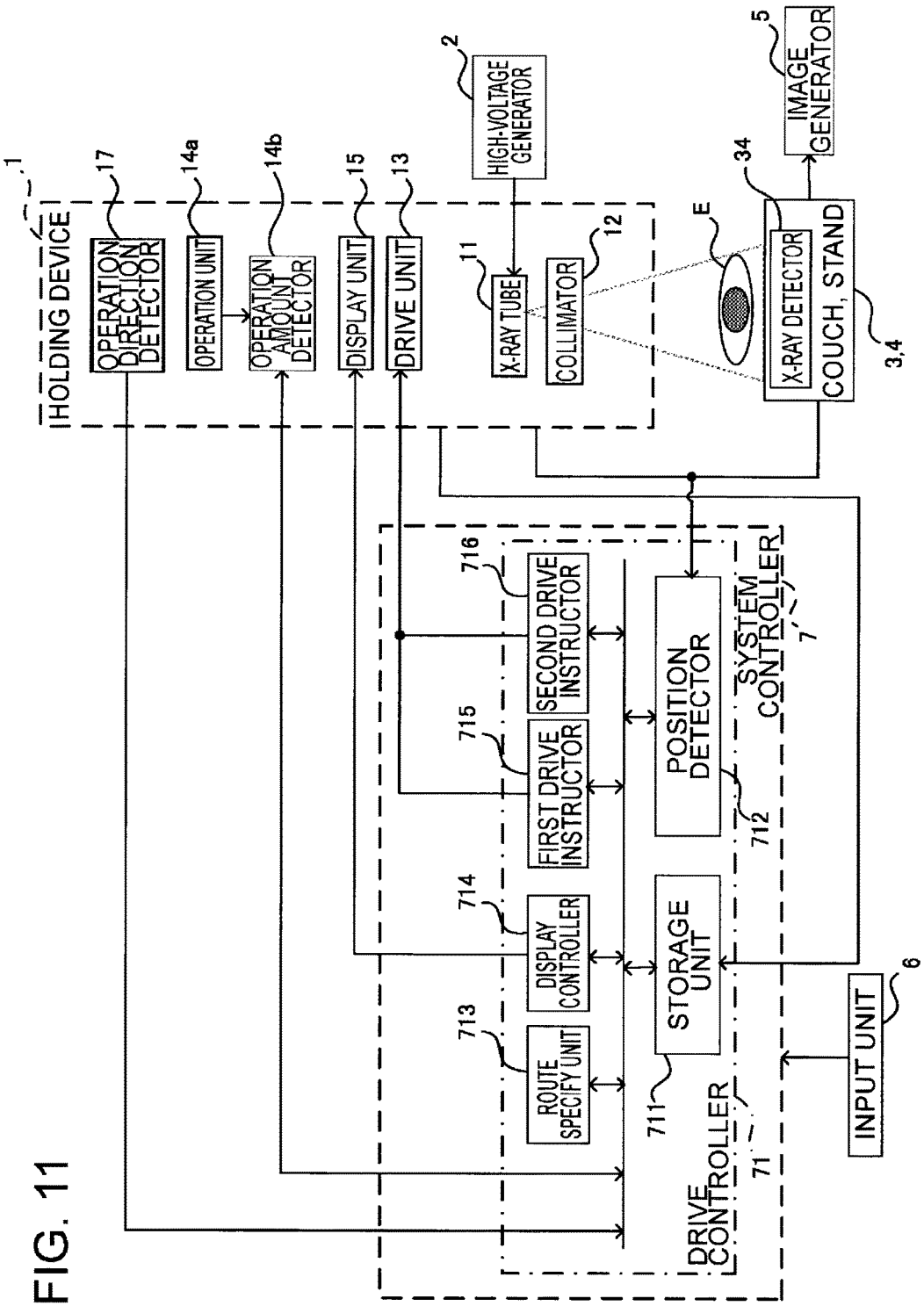
FIG. 11 is a block diagram of an X-ray diagnosis apparatus according to a second embodiment.

FIG. 11 is a block diagram of an X-ray diagnosis apparatus according to a second embodiment. The X-ray diagnosis apparatus of the second embodiment is configured to be capable of controlling a driving force based on the direction of moving operation. In the following, differences from the first embodiment are mainly described. The same explanation as given in the first embodiment may not be repeated.

The holding device 1 includes an operation direction detector 17. The operation direction detector 17 detects the direction of moving operation that the holding device 1 has received (a direction in which the holding device 1 is moved by the operation). Examples of the moving operation include pushing or pulling the operation handle H by the operator to manually move the holding device 1, and the like.

For example, the operation direction detector 17 includes a load detector device. The specific structure of the load detector device is designed to enable the detection of the direction of moving operation based upon general technologies. The load detector device is located in a position where the device can detect a load applied by moving operation. As examples of the position may be cited a position on the surface of the operation handle H, a position at the joint of the operation handle H and the housing of the holding device 1, and the like. With this, the operation direction detector 17 detects the direction of moving operation (operation direction) that the holding device 1 has received. The operation direction detector 17 feeds the first drive instructor 715 with operation direction information that indicates the detected operation direction.

The first drive instructor 715 checks the operation direction indicated by the operation direction information from the operation direction detector 17 with a movement direction indicated by movement direction information from the route specify unit 713. Thereby, the first drive instructor 715 determines whether the operation direction differs from the movement direction. Upon this determination, for example, the first drive instructor 715 obtains a difference between the operation direction and the movement direction. When the difference is equal to or larger than a predetermined threshold, the first drive instructor 715 determines that the operation direction is different from the movement direction. On the other hand, when the difference is less than the predetermined threshold, the first drive instructor 715 determines that the operation direction is the same as the movement direction. The predetermined threshold is designed in advance. A general vector calculation method is employed to calculate the difference between the operation direction and the movement direction.

Having determined that the operation direction differs from the movement direction, that is, the operation direction differs from the direction of a movement route, the first drive instructor 715 controls the drive unit 13 to stop the driving force. Specifically, the first drive instructor 715 sends an instruction signal to the drive unit 13 to stop the driving force. In response to the instruction signal, the drive unit 13 disconnects the clutches to stop the driving force.

Having determined that the operation direction matches the movement direction, that is, the operation direction is the same as the direction of a movement route, the first drive instructor 715 controls the driving force of the drive unit 13 according to an operation amount detected by the operation amount detector 14b. More specifically, while the operation amount is in a predetermined range, the first drive instructor 715 controls the drive unit 13 to output a driving force to move the holding device 1 toward the movement direction. In addition, when the operation amount falls out of the predetermined range, the first drive instructor 715 controls the drive unit 13 to stop the driving force.

[Operation]

Figure 12:
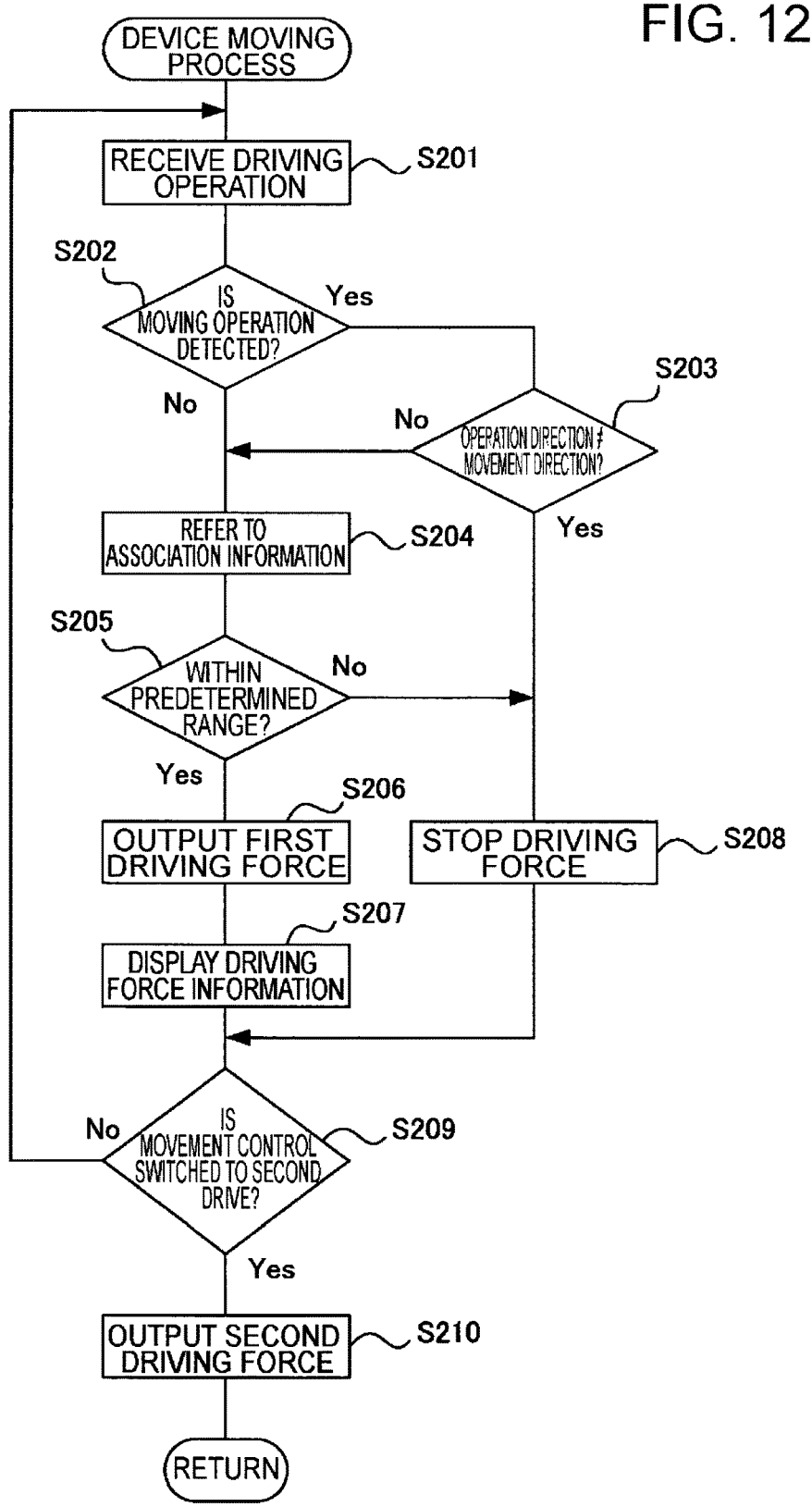
FIG. 12 is a flowchart of the operation of the X-ray diagnosis apparatus of the second embodiment.

FIG. 12 is a flowchart of the operation of the X-ray diagnosis apparatus of the second embodiment. The X-ray diagnosis apparatus of this embodiment operates in a similar manner as in the first embodiment except the device moving process (step S002 in FIG. 6 and FIG. 7), which is replaced by steps illustrated in FIG. 12.

(Step S201)

The operation unit 14a receives operator's driving operation. The operation amount detector 14b detects an operation amount indicating the strength of the driving operation received. The operation amount detector 14b outputs the detected operation amount to the first drive instructor 715.

(Step S202)

Having detected the direction of moving operation (Yes in step S202), the operation direction detector 17 feeds the first drive instructor 715 with operation direction information that indicates the detected direction of the moving operation (operation direction). If the operation direction detector 17 does not detect the direction of moving operation (No in step S202), the process moves to step S204.

(Step S203)

The first drive instructor 715 determines whether the operation direction differs from the movement direction. When the operation direction differs from the movement direction (Yes in step S203), the process moves to step S208. On the other hand, when the operation direction matches the movement direction (No in step S203), the process moves to step S204.

(Step S204 to S210)

Steps S204 to S210 are performed in the same manner as described above for steps S102 to S108 in FIG. 7.

According to the second embodiment, the X-ray diagnosis apparatus includes the holding device 1, the drive unit 13, the route specify unit 713, the operation direction detector 17, and the drive controller 71. The holding device 1 holds the X-ray tube 11, and is configured to be movable. The drive unit 13 is configured to be capable of moving the holding device 1. The route specify unit 713 specifies a movement route from the current position of the holding device 1 to the target position. The operation direction detector 17 detects the direction of moving operation (operation direction) that the holding device 1 has received. When the operation direction differs from the direction of the movement route, the drive controller 71 controls the drive unit 13 to stop the driving force. In this manner, when the direction of moving operation is different from the direction of the movement route, the X-ray diagnosis apparatus of this embodiment stops the driving force. For example, if an obstacle such as peripheral equipment is situated in the middle of the movement route, the operator may move the holding device 1 in a direction deviated from the movement route. On such an occasion, the driving force is halted to allow the operator to manually move the holding device 1. Besides, the operator can move the holding device 1 with a desired driving force while adjusting the pressing force on the button switch of the operation unit 14a. Thus, the positioning of the holding device 1 is facilitated.

According to the embodiments, the holding device is moved by a driving force controlled according to the strength of driving operation or the direction of moving operation. Thus, the positioning of the holding device is facilitated.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnosis apparatus, comprising:
   a holding device configured to be movable by a moving operation and hold an X-ray tube;
   a route specify unit configured to specify a movement route;
   a drive unit configured to drive the holding device along the specified movement route;
   an operation direction detector configured to detect an operation direction, the operation direction being a direction of the moving operation that the holding device has received; and a drive controller configured to control the drive unit to stop a driving force when the operation direction differs from a movement direction, the movement direction being a direction of the movement route,
wherein the holding device is further configured to receive the moving operation when the drive controller controls the drive unit to stop driving.

2. The X-ray diagnosis apparatus of claim 1, wherein the drive controller includes
a storage unit configured to store a target position, and
a position detector configured to detect a current position, and
the route specify unit is configured to specify the movement route based on the current position detected by the position detector and the target position.

3. The X-ray diagnosis apparatus of claim 1, further comprising an operation amount detector configured to detect an operation amount indicating strength of driving operation, the driving operation being an operation for controlling the driving force, wherein
the drive controller is configured to store a predetermined range, and control the drive unit to stop the driving force when the operation amount falls out of the predetermined range.

4. The X-ray diagnosis apparatus of claim 3, wherein the drive controller is configured to control the drive unit to output the driving force to move the holding device in the movement direction while the operation amount is in the predetermined range.

5. The X-ray diagnosis apparatus of claim 3, wherein the drive controller is configured to store, in advance, association information that associates the operation amount with the driving force in a proportional relationship in the predetermined range, and
the drive controller is further configured to control the drive unit to output the driving force associated with the operation amount based on the association information while the operation amount is in the predetermined range.

6. The X-ray diagnosis apparatus of claim 5, wherein the drive controller is configured to store, in advance, the association information with respect to each operator ID that uniquely identifies an operator, and
the drive controller is further configured to control the drive unit based on the association information for an operator ID of interest while the operation amount is in the predetermined range.

7. The X-ray diagnosis apparatus of claim 5, wherein the drive controller includes an association information change unit configured to change the association information to obtain new association information upon receipt of change operation for changing the association information, and
the drive controller is configured to control the drive unit based on the new association information obtained by the association information change unit while the operation amount is in the predetermined range.

8. The X-ray diagnosis apparatus of claim 1, wherein the holding device includes a display unit, and
the drive controller is configured to display movement direction information indicating the movement direction on the display unit.

9. The X-ray diagnosis apparatus of claim 1, wherein the holding device includes a display unit, and
the drive controller is configured to display driving force information indicating magnitude of the driving force on the display unit.

10. The X-ray diagnosis apparatus of claim 1, wherein the operation direction detector includes a load detector device detecting the operation direction, which is the direction of the moving operation that the holding device has received.

11. An X-ray diagnosis apparatus, comprising:
a holding device configured to be movable by a moving operation and hold an X-ray tube;
a drive unit configured to be capable of moving the holding device;
an operation amount detector configured to detect an operation amount indicating strength of operation when the holding device is operated; and
a drive controller configured to control driving force of the drive unit based on the operation amount, wherein
the drive controller is further configured to control the driving force of the drive unit based on the operation amount when the operation amount is in a predetermined range, and control the drive unit to stop driving when the operation amount exceeds an upper limit of the predetermined range, and
the holding device is further configured to receive manual moving operation when the drive controller controls the drive unit to stop driving.

* * * * *